United States Patent
Ma et al.

(10) Patent No.: US 7,462,753 B2
(45) Date of Patent: Dec. 9, 2008

(54) NANO-SILVER WOUND DRESSING

(75) Inventors: Rin-Hsiung Ma, Longtan Township, Taoyuan County (TW); Yi-Hsiuan Yu, Longtan Township, Taoyuan County (TW)

(73) Assignee: Chung Shan Institute of Science and Technology, Armaments Bureau, M.N.D., Taoyuan County (TW)

( * ) Notice: Subject to any disclaimer, the term of this patent is extended or adjusted under 35 U.S.C. 154(b) by 121 days.

(21) Appl. No.: 11/455,188

(22) Filed: Jun. 19, 2006

(65) Prior Publication Data

US 2007/0293799 A1 Dec. 20, 2007

(51) Int. Cl.
*A61F 13/00* (2006.01)

(52) U.S. Cl. .......................................... 602/48; 602/53

(58) Field of Classification Search ............. 602/41–59; 424/443–449; 604/304–308; 128/888, 889
See application file for complete search history.

(56) References Cited

U.S. PATENT DOCUMENTS 2,077,299 A * 4/1937 Abrams et al. ............. 604/304
4,529,623 A * 7/1985 Maggs ....................... 427/227
4,928,681 A * 5/1990 Langston et al. .............. 602/58
5,244,457 A * 9/1993 Karami et al. ................. 602/55
2004/0078015 A1* 4/2004 Copat et al. .................. 604/370
2004/0211053 A1* 10/2004 Trainer et al. .............. 29/623.1
2006/0057369 A1* 3/2006 Hilfenhaus et al. .......... 428/343

* cited by examiner

*Primary Examiner*—Kim M Lewis
(74) *Attorney, Agent, or Firm*—Rosenberg, Klein & Lee

(57) ABSTRACT

A nano-silver wound dressing consisting of a skin contact layer made from hydrophilic cloth and directly contacting a wound on the surface of the skin, a disinfecting (or bactericidal) antitoxic layer made from activated charcoal cloth impregnated with nanocrystalline silver, a blood absorbing and styptic layer made from a superabsorbent polymer nonwoven cloth, an isolation layer made from a composite fabric with a pore size of less than 5 μm, and an elastic bandage for fixing a main body on the site of wound. Edges of the isolation layer and the skin contact layer are integrated to form a main body while the disinfecting (or bactericidal) antitoxic layer as well as the blood absorbing and styptic layer are separated from each other and both enclosed inside the main body.

11 Claims, 1 Drawing Sheet

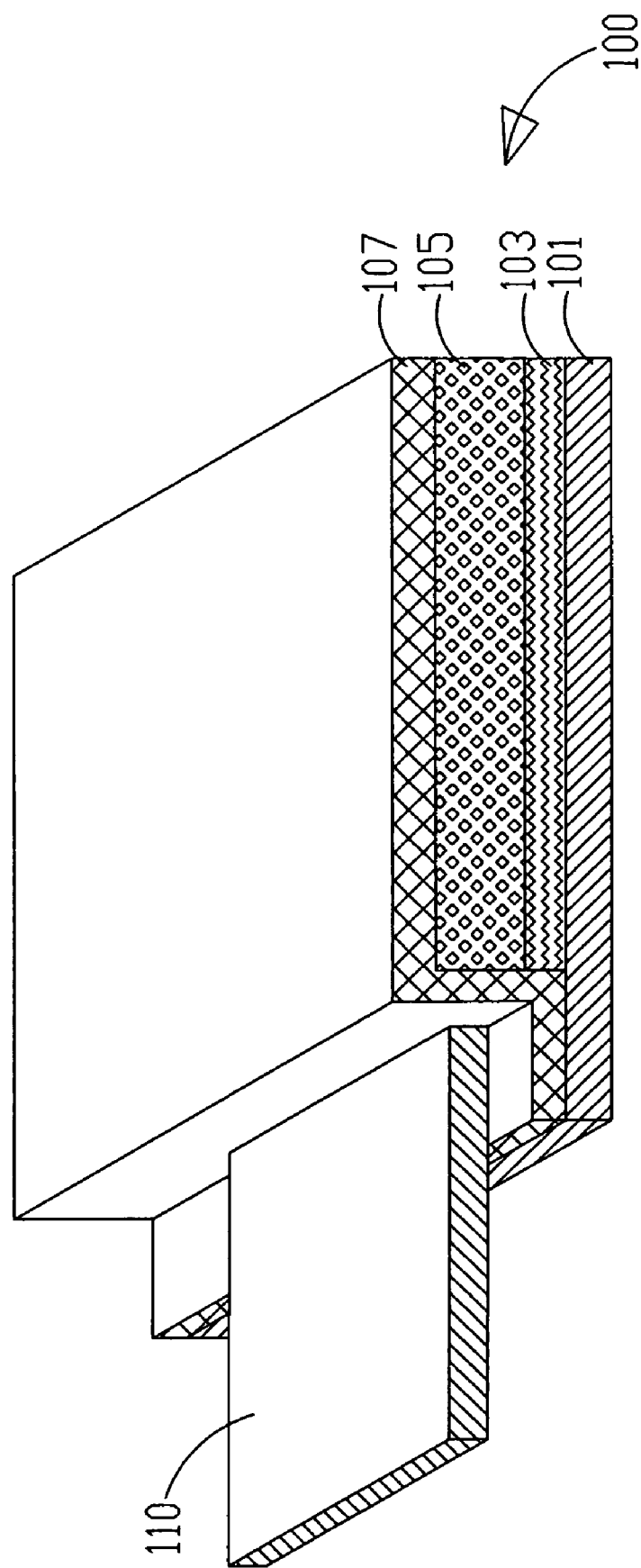

NANO-SILVER WOUND DRESSING

BACKGROUND OF THE INVENTION

The present invention relates to a wound dressing, especially to a nano-silver wound dressing.

Silver has been used as a bactericidal agent for a long time. Silver works as an antimicrobial through a number of pathways. It acts on the cell wall so as to inhibit cell wall replication. Silver can also inactivate cellular respiratory chain and block energy supply of cells, or directly act on nucleic acids such as RNA and DNA. With those functions, the bacterium is either inhibited from replication or is killed. Because silver affects so many sites within cells, it has antimicrobial activity against multiple micro-organisms including bacteria, virus and fungi. In the past, most of silver being used is silver salt such as silver nitrate. However, it's highly toxic so that they are not as practical as chemical bactericides or antibiotics. However, due to antibiotic abuse, a broad spectrum of bacteria has become resistant to antibiotics. As to bactericidal agents for external use, they may have toxicity for human tissue cells. Moreover, they can only fight against certain bacteria; it is not effective for over 500 species of bacteria.

In recent years, nano-silver technology has been a research trend. Nanocrystalline silver results in a very large specific surface area for the release of ionic silver. Even only a small amount of silver provides a bactericidal action. Moreover, the silver ion is released into the wound for long-lasting bactericidal effect in a controlled fashion. It's economic and effective. Furthermore, the development of antimicrobial resistance to silver would be extremely rare and the silver further enhances wound healing. Therefore, the silver has been hot since the new century. For example, American medical products such as Acticoat produced by Smith & Nephew Co. and Silverlon produced by Argentum Medical, LLC are silver-coated wound dressings. They invest a lot of money and labor on various kind of tests such as tests of skin irritation, skin toxicity, cytotoxicity, hemolysis, systemic toxicity, and carcinogenicity, damages to liver, kidney and blood, antimicrobial activity against various bacteria, fungi and virus, wound healing test, and so on. The wound dressings have been approved by the FDA (food and drug administration). Besides the above two dressings for wounds and burns Silvasorb of Medline Co., Aquacel of Convatec Co., Arglaes of Medline Co., and Contreet of Coloplast Co. are all non-woven dressings with nanocrystalline silver. The release of the silver ion is in a controlled fashion and with long-lasting efficacy. The dressing can be left in place for seven days without replacement.

As to wound dressing made from activated carbon fiber with silver, it is quite rare as only one product-Actisorb of American Johnson & Johnson company is available. It consists principally of activated carbon impregnated with metallic silver produced by heating a specially treated fine viscose fabric under carefully controlled conditions, but it has no hemostatic function. Refer to GB2206495A, this is a military hemostatic and antitoxic dressing made by activated charcoal cloth fabric and absorbent gauze. However, due to capillary action of the absorbent cotton, it may have problems of blood leaking with poor blood staunching function, it is not antibacterial dressing. Only a disinfected, antitoxic dressing disclosed in Taiwanese Utility patent No. 114129 has all three features disinfection, antitoxicity and blood staunching. In this patent, the absorbent cotton is replaced by Superabsorbent Polymer (SAP) whose volume is enlarged after absorbing blood so as to make the bandage have adverse pressure, pressing on the wound site for better blood staunching effect. Moreover, the activated carbon fiber with silver treated by a heating process is used to achieve antitoxic and disinfected effects.

However, the carbon fiber with silver pretreated by a heating process can only be produced by large-scale factory such as charcoal cloth company in United Kingdom and the price is quite expensive-about $ NT150 dollars per 10 square centimeters with the amount of silver 3 weight percent (wt. %).

SUMMARY OF THE INVENTION

Therefore, it is a primary object of the present invention to provide a nano-silver wound dressing for solving the problem of high manufacturing cost of silver pretreated activated charcoal cloth.

In order to achieve the above object, a nano-silver wound dressing according to the present invention includes a skin contact layer, a disinfective (or bactericidal) antitoxic layer, a blood absorbing and styptic layer, an isolation layer, and an elastic bandage. The skin contact layer made from hydrophilic nonwoven contacts wound site on skin surface directly. The disinfected antitoxic layer is made from activated charcoal cloth impregnated with nanocrystalline silver. And the blood absorbing and styptic layer is made from SAP nonwoven with pore size less than 5 micrometer ($\mu m$) and is connected with edges of the skin contact layer to form a main body. The disinfected antitoxic layer and the blood absorbing and styptic layer are separated with each other and are enclosed inside the main body. The elastic bandage is joined with the main body for fixing the main body on the wound site.

In an embodiment of a nano-silver wound dressing according to the present invention, the minimum amount of nanocrystalline silver impregnated inside the activated charcoal cloth is 0.1-3 wt. % while the diameter of the nanocrystalline silver ranges from 1 to 100 nanometer (nm).

In an embodiment of a nano-silver wound dressing according to the present invention, the amount of SAP ranges from 5 to 50 wt. % and the SAP is acrylic acid—starch grafted copolymer sodium salt.

In an embodiment of a nano-silver wound dressing according to the present invention, the above composite fabric can be SMS composite nonwoven, that is spunbond-meltblown-spunbond three-layer fabric, it also can be polyester/cotton blended fabrics with water and oil repellency, or other suitable fabrics.

According to a preferred embodiment of the present invention, the above hydrophilic cloth includes hydrophilic nonwoven cloth.

According to a preferred embodiment of the present invention, the above elastic bandage includes medical bandage or non-woven elastic bandage.

According to a preferred embodiment of the present invention, the above way for connecting edges of the isolation layer and the skin contact layer includes heat fusion or sewing.

According to a preferred embodiment of the present invention, the above way of joining the elastic bandage with the main body includes heat fusion or sewing.

The activated charcoal cloth used by the present invention is treated by impregnation of nanocrystalline silver, different from conventional charcoal cloth with silver being treated with a heating process. Thus the manufacturing cost of wound dressings is reduced. Moreover, due to the activated charcoal cloth impregnated with silver, the present invention has bactericidal and antitoxic functions. Furthermore, the absorbent cotton is replaced by SAP so that the problem of blood leaking is improved. In addition, the volume of the non-woven cloth with SAP is increased after absorbing blood so as to make the elastic bandage have adverse pressure, pressing on the wound site to achieve better effect of stopping bleeding.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein The FIGURE is a schematic drawing showing a cross section of an embodiment in accordance with the present invention.

DETAILED DESCRIPTION OF THE PREFERRED EMBODIMENT

Refer to the FIGURE, a nano-silver wound dressing in accordance with the present invention from inside to outside includes a skin contact layer 101 that is a hydrophilic cloth contacting wound on surface of skin, a disinfected antitoxic layer 103 made from activated charcoal cloth impregnated with nanocrystalline silver, a blood absorbing and styptic layer 105 made from non-woven cloth with SAP, and an isolation layer 107 made from composite fabric with pores whose diameter is less than 5 μm. Edges of the isolation layer 107 and the skin contact layer 101 are sealed to form a main body 100. The way of sealing are sewing or heated to fusion. The disinfected antitoxic layer 103 and the blood absorbing and styptic layer 105 are separated from each other and both enclosed inside the main body 100. Moreover, an elastic bandage 110 connected with the main body 100 for fixing the main body 100 on the site of wound. The elastic bandage 110 is joined with the main body 100 by sewing or heat fusion. The elastic bandage 110 can be medical bandage or non-woven elastic bandage.

The skin contact layer 101 is made from hydrophilic cloth such as hydrophilic non-woven cloth with features of high water absorption and rapid transport of liquids. Through the EDANA (European Association of Non-woven Manufacturers) Liquid strike-through time 150.2 (1993) and Coverstock wetback (1993) tests for textile, it is proven that the fabrics provide dry skin contact and increased wearing comfort.

The disinfected antitoxic layer 103 made from activated charcoal cloth impregnated with nanocrystalline silver contains 0.1-3 wt. %. while the diameter of the nanocrystalline silver ranges from 15 to 50 nm. The charcoal cloth itself has no germicidal effect. The present invention uses wet chemical method to treat the activated charcoal cloth, impregnated with nanocrystalline silver so as to have bactericidal effect and easy processing. There is no need to manufacture the products by a heating process in large charcoal cloth factory. The present invention can be mass-produced in small and medium-sized factories. Thus the present invention reduces manufacturing cost of wound dressings.

Moreover, the amount of nanocrystalline silver inside the silver-impregnated activated charcoal cloth according to the present invention is adjustable, Within the dressing, 0.5 wt. % nanocrystalline silver provides good bactericidal effect. Compared with the activated charcoal cloth with silver produced by Charcoal cloth company, UK that contains 3 wt. %, the manufacturing cost of the wound dressings is reduced due to few raw material being used.

Furthermore, the silver inside the silver-impregnated activated charcoal cloth according to the present invention silver ion is released in a controlled fashion—ranging from 1 to 20 ppm (parts per million) with good bactericidal effect. Thus the present invention has continued antimicrobial activity, lasting for over a week.

The amount of SAP inside the blood absorbing and styptic layer 105 ranges from 5 to 50 wt. %, preferably from 10 to 30 wt. %. SAP can be acrylic acid-starch grafted copolymer sodium salt. The present invention uses non-woven cloth with SAP to replace absorbent cotton. Thus the shortcoming of blood leaking caused by capillary action of the absorbent cotton is improved. Furthermore, the volume of the non-woven cloth with SAP-according to the present invention is increased after absorbing blood at the wound site so as to make the elastic bandage have adverse pressure, pressing on the wound site to achieve better effect to halt bleeding.

Composite fabric is SMS composite non-woven fabric spunbond-meltblown-spunbond, polyester/cotton blended fabrics has water and oil repellency , or other suitable fabrics. The pore size of composite fabrics is less than 5 μm, preferably from 2 to 3 μm. The SMS composite non-woven cloth provides a barrier to bacterial penetration, with good air-permeability and liquid-proofing characters.

In order to demonstrate excellent effects of a nano-silver wound dressing in accordance with the present invention, the following two embodiments are examined and compared by various tests:

Embodiment 1 the skin contact layer (the inner layer): hydrophilic non-woven cloth the disinfected antitoxic layer: nanocrystalline silver-impregnated activated charcoal cloth the blood absorbing and styptic layer: non-woven cloth having 5-50 wt. % SAP the isolation layer (the outer layer): SMS composite fabric with a pore size of 3 μm The above layers are separated from one another. Edges of the skin contact layer and the isolation layer are heated and fused to form a main body. The main body is a square with side ranging from 15 to 30 cm or a rectangle whose width ranges from 10 to 20 cm and length ranges from 15 to 30 cm with thickness of 0.4 cm. The main body is joined with the elastic bandage whose width is 10 cm and the length is 500 cm by heat fusion.

Embodiment 2 the skin contact layer (the inner layer): hydrophilic non-woven cloth the disinfected antitoxic layer: nanocyrstalline silver-impregnated activated charcoal cloth the blood absorbing and styptic layer: non-woven cloth having 5-50 wt. % SAP the isolation layer (the outer layer): polyester/cotton blended fabrics with water and oil repellency.

The above layers are separated from one another. Edges of the skin contact layer and the isolation layer are sewed to form a main body. The main body is a square with side ranging from 15 to 30 cm or a rectangle whose width ranges from 10 to 20 cm and length ranges from 15 to 30 cm with thickness of 0.4 cm. The main body is joined with the elastic bandage whose width is 10 cm and the length is 500 cm by sewing.

Test 1 Antitoxic Test

According to S.D. test method (Static Diffusion test) of MIL-STD-282, organic phosphorous compounds and organic sulfides are used for measurement of penetration resistance. For the embodiment 1 and embodiment 2, the penetration resistance are both over 24 hours. While qualified standard for Chinese military specification CMS-A-20689 is 24 hours.

Test 2 Bactericidal Test

While the activated charcoal cloth impregnated with nanocrystalline silver in embodiment 1 and embodiment 2, both have good antimicrobial activity (AATCC 100-2004) and efficacy 99.99% against *Staphylococcus aureus* and *Escherichia coli*.

Test 3 Hemostatic Test

According to ASTM-1117-80 and CNS (Chinese National Standard) 9325-90 test methods for absorption of sanitary napkins, the embodiment 1 and embodiment 2 are able to absorb 30 times its own weight of water and Congo Red Solution while the absorbent cotton only absorbs 15 times.

In summary, a nanocrystalline silver wound dressing according to the present invention has following advantages:

1. The dressing has been tested by domestic and international standards, proven to provide excellent antitoxic effect, bactericidal effect and blood staunching capability.
2. The present invention is identified to provide dry and comfortable skin contact.
3. The silver-impregnated activated charcoal cloth of the present invention is easy to be processed, without being treated by a heating process in large-scale charcoal cloth factories. It can be mass-produced in small or medium-sized factories. Thus the manufacturing cost of the dressings can be reduced.
4. The amount of nanocrystalline silver inside the activated charcoal cloth according to the present invention is adjustable. Only 0.5 wt. % silver has good bactericidal effect. The fewer amount of raw material leads to lower manufacturing cost of the dressings.
5. The activated charcoal cloth impregnated with silver of the present invention can last anti-microbial effects for 7 days or more.
6. The isolation layer of the present invention is proven to have good air-permeability.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A nano-silver wound dressing comprising:
   a first skin contact layer wherein said skin contact layer is formed of hydrophilic cloth, contacting a wound site on the skin directly;
   a second disinfecting (or bactericidal) antitoxic layer mounted contiguously on top of said first skin contact layer wherein said disinfecting antitoxic layer is formed of activated charcoal cloth impregnated with nanocrystalline silver;
   a third blood absorbing and styptic layer mounted contiguously on top of said second disinfecting antitoxic layer wherein said blood absorbing and styptic layer is formed of a superabsorbent polymer (SAP) non-woven cloth, said SAP for expanding with blood absorption and simultaneously increasing a contact pressure on said wound by said nano-silver wound dressing wherein said SAP increases in weight with said blood absorption;
   a fourth isolation layer mounted contiguously on top of said third blood absorbing and styptic layer wherein said isolation layer is formed of a composite fabric with a pore size less than 5 μm, and is connected to the edges of the skin contact layer to form a main body for enclosing the disinfected antitoxic layer and the blood absorbing and styptic layer; and
   an elastic bandage connecting with the main body for fixing the main body on wound site.

2. The nano-silver wound dressing as claimed in claim 1, wherein the amount of nanocrystalline silver inside the activated charcoal cloth is 0.1-3 wt. %.

3. The nano-silver wound dressing as claimed in claim 2, wherein the particle size of the nanocrystalline silver ranges from 1 to 100 nm.

4. The nano-silver wound dressing as claimed in claim 1, wherein the amount of SAP ranges from 5 to 50 wt. %.

5. The nano-silver wound dressing as claimed in claim 1, wherein said SAP is acrylic acid-starch grafted copolymer sodium salt.

6. The nano-silver wound dressing as claimed in claim 1, wherein the pore size of the composite fabric ranges from 2 to 5 μm.

7. The nano-silver wound dressing as claimed in claim 1, wherein the composite fabric has a spunbound-meltblown-spunbound (SMS) composite nonwovens or polyester/cotton cloth with water and oil repellency.

8. The nano-silver wound dressing as claimed in claim 1, wherein the hydrophilic cloth includes hydrophilic non-woven cloth.

9. The nano-silver wound dressing as claimed in claim 1, wherein the elastic bandage having medical bandage or non-woven elastic bandage.

10. The nano-silver wound dressing as claimed in claim 1, wherein the way for connecting edges of the isolation layer and the skin contact layer includes heat fusion or sewing.

11. The nano-silver wound dressing as claimed in claim 1, wherein the way for connecting the elastic bandage with the main body includes heat fusion or sewing.

* * * * *